United States Patent
Inoue et al.

(10) Patent No.: US 10,114,032 B2
(45) Date of Patent: Oct. 30, 2018

(54) BLOOD COAGULATION TEST METHOD

(71) Applicant: NIPPON TELEGRAPH AND TELEPHONE CORPORATION, Tokyo (JP)

(72) Inventors: Suzuyo Inoue, Tokyo (JP); Katsuyoshi Hayashi, Tokyo (JP); Yuzuru Iwasaki, Tokyo (JP); Tsutomu Horiuchi, Tokyo (JP); Nobuaki Matsuura, Tokyo (JP); Emi Tamechika, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 0 days.

(21) Appl. No.: 14/891,909

(22) PCT Filed: May 21, 2014

(86) PCT No.: PCT/JP2014/063431
§ 371 (c)(1),
(2) Date: Nov. 17, 2015

(87) PCT Pub. No.: WO2014/189067
PCT Pub. Date: Nov. 27, 2014

(65) Prior Publication Data
US 2016/0116491 A1 Apr. 28, 2016

(30) Foreign Application Priority Data
May 23, 2013 (JP) .................................. 2013-108947

(51) Int. Cl.
*G01N 33/86* (2006.01)
*G01N 21/41* (2006.01)
*G01N 33/49* (2006.01)

(52) U.S. Cl.
CPC ............. *G01N 33/86* (2013.01); *G01N 21/41* (2013.01); *G01N 33/4905* (2013.01)

(58) Field of Classification Search
CPC ............................... G01N 33/86; G01N 21/41
See application file for complete search history.

(56) References Cited

U.S. PATENT DOCUMENTS

2010/0103421 A1* 4/2010 Johansen ............. G01N 21/553
356/367

FOREIGN PATENT DOCUMENTS

| JP | 06-027115 A | 2/1994 |
| JP | H09-502800 A | 3/1997 |

(Continued)

OTHER PUBLICATIONS

Blood Coagulation Testing Method Based on Flow Velocity Measurement using a Surface Plasmon Resonance Based Microfluidic Device Katsuyoshi Hayashi, Suzuyo Inoue, Yuzuru Iwasaki, Michiko Seyama, Tsutomu Horiuchi and Emi Tamechika 16th International Conference on Miniaturized Systems for Chemistry and Life Sciences. Oct. 28-Nov. 1, 2012.*

(Continued)

*Primary Examiner* — Krishnan S Menon
*Assistant Examiner* — Dwan A Gerido
(74) *Attorney, Agent, or Firm* — Womble Bond Dickinson (US) LLP

(57) ABSTRACT

In step S101, a specimen containing blood plasma and a coagulation activating agent are introduced into a flow channel, with the coagulation activating agent being positioned ahead, in a state in which portions arrayed in series in the extending direction of the flow channel flow in contact with each other. In step S102, in the process in which the coagulation activating agent, the contact region between the coagulation activating agent and the specimen, and the (Continued)

specimen pass through a measurement portion provided midway along the flow channel in the order named, the refractive indices of the coagulation activating agent and the contact region are measured in a time-series manner. In step S103, the blood coagulation ability of the specimen is measured by comparing the first refractive index value which is the refractive index of the coagulation activating agent with the second refractive index value which is the minimum refractive index of the contact region.

2 Claims, 6 Drawing Sheets

(56) References Cited

FOREIGN PATENT DOCUMENTS

| JP | 09-266798 A | 10/1997 |
|----|----|----|
| JP | 2003-232725 A | 8/2003 |
| JP | 2009-506332 A | 2/2009 |
| JP | 2010-133727 A | 6/2010 |
| JP | 2010-539503 A | 12/2010 |
| JP | 2011-232137 A | 11/2011 |
| JP | 2013-053959 A | 3/2013 |
| JP | 2013-257145 A | 12/2013 |
| JP | 2014-041041 A | 3/2014 |

OTHER PUBLICATIONS

Polymerization of Biological Molecules in a Microchannel Generates Both High and Low-Refractive Index Ingredients. K. Hayashi, S. Inoue, T. Horiuchiu, Y. Iwasaki, N. Matsuura, and Y. Sato 17th International Conference on Miniaturized Systems for Chemistry and Life Sciences Oct. 2013.*

Naya et al., "Highly Sensitive SPR Sensor Using a Monolithic Prism Tip",Fujifilm Research & Development, No. 50, pp. 51-54, 2005.

Hayashi, "Monitoring of Blood Coagulation Using a SPR based Microfluidic Sensor", Chemical sensors, vol. 29, Supplement B, Sep. 27, 2013, pp. 49-51.

Inoue et al., "Quick Blood Coagulation Measurement Method by Stop Flow SPR Measurement System", The 28th Conference Proceedings of the Society for Chemistry and Micro-Nano Systems, 2013.

* cited by examiner

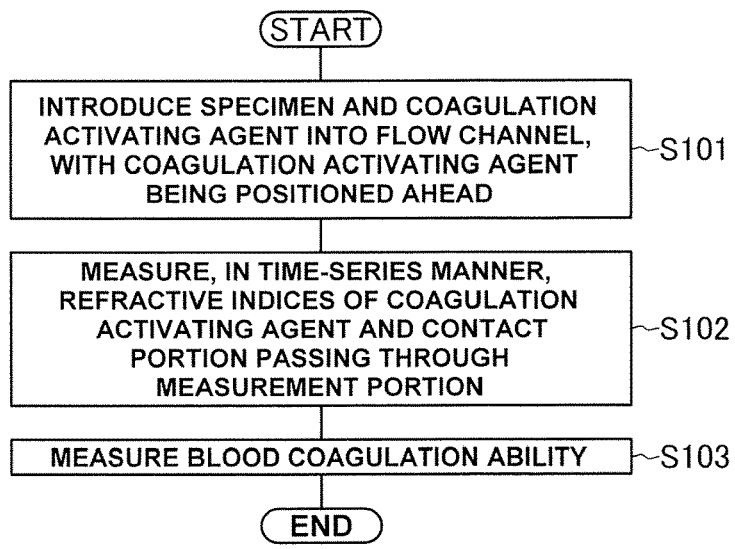
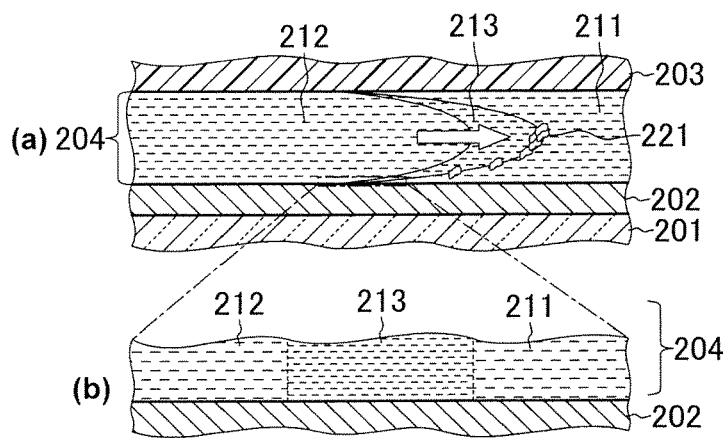
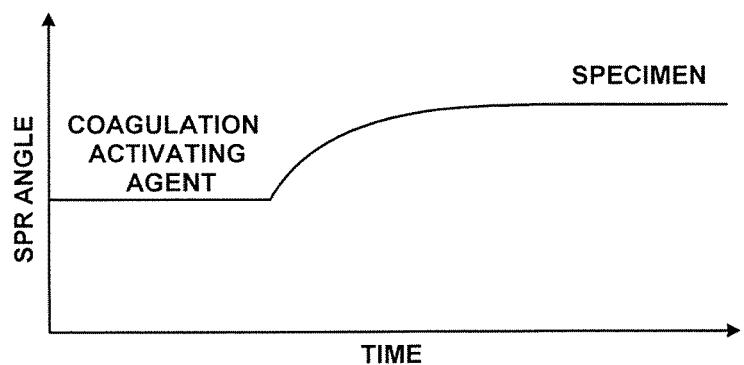

BLOOD COAGULATION TEST METHOD

TECHNICAL FIELD

The present invention relates to a blood coagulation test method of measuring the coagulation ability of blood or blood plasma.

BACKGROUND ART

Blood coagulation activity is an important item for obtaining an index used for screening the deficiency of an extrinsic coagulation factor or monitoring the abnormality of the liver function and an anticoagulant treatment with oral administration.

Such a blood coagulation test mainly uses a PT (Prothrombin time) measurement method, an APTT (Activated Partial Thromboplastin Time) measurement method, a fibrinogen test, and the like. These measurements and tests are executed by using large-sized analysis apparatuses in hospitals. When conducting a test by using the PT measurement method and the APTT measurement of these methods, a protein (thrombomodulin or ellagic acid) and calcium ions which coagulate blood are mainly mixed as coagulation reaction triggers in blood plasma, the time (coagulation point) from the start of mixture to the completion of coagulation is measured, and a delay time is estimated by comparing the measured time with a standard blood plasma result.

This PT method of measuring the blood coagulation activity of an endogenous/extrinsic blood coagulation route has currently been internationally standardized (PT-INR) and considered as a test item which is high in repeatability and reliability. For example, first of all, an agitation resistance scheme is available as a method of physically executing the PT method. The agitation resistance scheme is a method in which a sample (specimen) is introduced together with an activating agent, and a blood coagulation time is measured from a rise in agitation resistance when the sample and the agent are agitated with a fin.

In addition, as a method of executing the PT measurement method, there is available a light scattering method (see patent literatures 1, 2, and 3). The light scattering method is a method in which a blood plasma as a target is mixed with a reagent containing a component for promoting coagulation activation in a measurement vessel, light is caused to enter the vessel, and a blood coagulation time is measured by measuring a change in the amount of scattered light of the incident light. Methods of obtaining a blood coagulation time from the amount of scattered light include a method directly using the amount of scattered light, a method using the derivative value of the amount of scatted light, and a method of obtaining the time until the amount of scattered light reaches a predetermined value (see patent literature 1).

The above agitation resistance scheme and light scattering method are currently generally used for the test of blood coagulation in many cases. In addition to them, a heat conduction scheme, a crystal oscillator scheme, an aggregation measurement method using magnetic beads (see patent literature 4), and the like have been developed.

In addition, the present inventors have proposed a method of testing coagulation activity by measuring a flow velocity using an SPR (Surface Plasmon Resonance) measurement method using a chip having a micro flow channel. In this test, first of all, a blood plasma sample completely activated by being mixed with coagulation activating agents (ellagic acid and calcium chloride) is prepared immediately before measurement. Subsequently, the blood plasma sample is introduced into the flow channel filled in advance with a buffer solution to convert the flow velocity of blood plasma flowing in the flow channel into a coagulation time (see patent literature 5). Flow velocity measurement using such a micro flow channel has a merit that it can quickly measure coagulation activity by using a small amount of specimen.

RELATED ART LITERATURE

Patent Literature

Patent Literature 1: Japanese Patent Laid-Open No. 06-027115
Patent Literature 2: Japanese Patent Laid-Open No. 2009-506332
Patent Literature 3: Japanese Patent Laid-Open No. 09-266798
Patent Literature 4: Japanese Patent Laid-Open No. 09-502800
Patent Literature 5: Japanese Patent Laid-Open No. 2011-232137
Patent Literature 6: Japanese Patent Laid-Open No. 2010-133727

Non-Patent Literature

Non-Patent Literature 1: Masayuki NAYA et al., "Highly Sensitive SPR Sensor Using a Monolithic Prism Tip", FUJIFILM RESEARCH & DEVELOPMENT, NO. 50, pp. 51-54, 2005

Disclosure of Invention

Problem to be Solved by the Invention

The above blood coagulation test based on flow velocities, however, cannot conduct an accurate test. In a blood coagulation test, after a coagulation activating substance is generated in blood plasma by using a coagulation activating agent, a change in flow velocity due to a viscosity increase caused by a coagulated substance mainly formed from fibrin is measured. For this reason, insolubilized protein is non-specifically adsorbed in the measurement vessel used for the measurement to contaminate its surface. In particular, fibrin is a protein having a molecular weight large enough to allow simultaneous interaction among protein residues, and hence has higher nonspecific adsorption power than other proteins.

As described above, in a blood coagulation test, since the flow channel used for a test is internally contaminated, the contamination will change the flow velocity. A change in flow velocity due to contamination causes a large measurement error, resulting in failure to obtain an accurate measurement value. In order to solve this problem, for example, the interior of the flow channel may be cleaned to always keep the interior of the flow channel uniformly clean. Such cleaning techniques include, for example, a method by filling the interior of the flow channel with or immersing each micro flow channel chip in a protein removing solution such as an alkaline cleaning solution and a method, as a physical technique, using a combination of cleaning solution spraying, ultrasonic cleaning, and the like (see patent literature 6).

However, since no test can be conducted during cleaning, when, for example, a plurality of tests are consecutively conducted, the test throughput greatly decreases. In addition, the technique of conducting a blood coagulation test by measuring a flow velocity is designed to measure a flow velocity dependent on viscosity. For this reason, when measuring specimens having the same coagulation ability but having different viscosities, it is impossible to correctly discriminate these coagulation abilities.

As described above, a blood coagulation test using a micro flow channel has a merit that it can quickly measure coagulation activity by using a small amount of specimen. However, using flow velocities will raise the problem that it is impossible to conduct an accurate test.

The present invention has been made to solve the above problems, and has as its object to more accurately test blood coagulation ability by a blood coagulation test using a micro flow channel.

Means of Solution to the Problem

A blood coagulation test method according to the present invention includes a first step of introducing a specimen containing blood plasma and a coagulation activating agent into a flow channel, with the coagulation activating agent being positioned ahead, in a state in which portions arrayed in series in an extending direction of the flow channel flow in contact with each other, a second step of measuring refractive indices of the coagulation activating agent and a contact region between the coagulation activating agent and the specimen in a time-series manner in the process in which the coagulation activating agent, the contact region, and the specimen pass through a measurement portion provided midway along the flow channel in the order named, and a third step of measuring blood coagulation ability of the specimen by comparing a first refractive index value which is the measured refractive index of the coagulation activating agent with a second refractive index value which is a measured minimum refractive index of the contact region. Note that a surface plasmon resonance angle measured by surface plasmon resonance measured at the measurement portion is preferably used as the refractive index value.

Effects of the Invention

As described above, according to the present invention, it is possible to obtain an excellent effect of being able to more accurately test blood coagulation ability by a blood coagulation test using a micro flow channel.

BRIEF DESCRIPTION OF DRAWINGS

FIG. 1 is a flowchart for explaining a blood coagulation test method according to an embodiment of the present invention;

FIG. 2 is a view for explaining how a coagulation activating agent 211 and a specimen 212 flow in a micro flow channel 204 formed between a substrate 201 and a flow channel substrate 203;

FIG. 3 is a graph showing a change in refractive index measured while the coagulation activating agent 211 and the specimen 212 flow in the micro flow channel 204 when no coagulation reaction occurs;

BEST MODE FOR CARRYING OUT THE INVENTION

Figure 4:
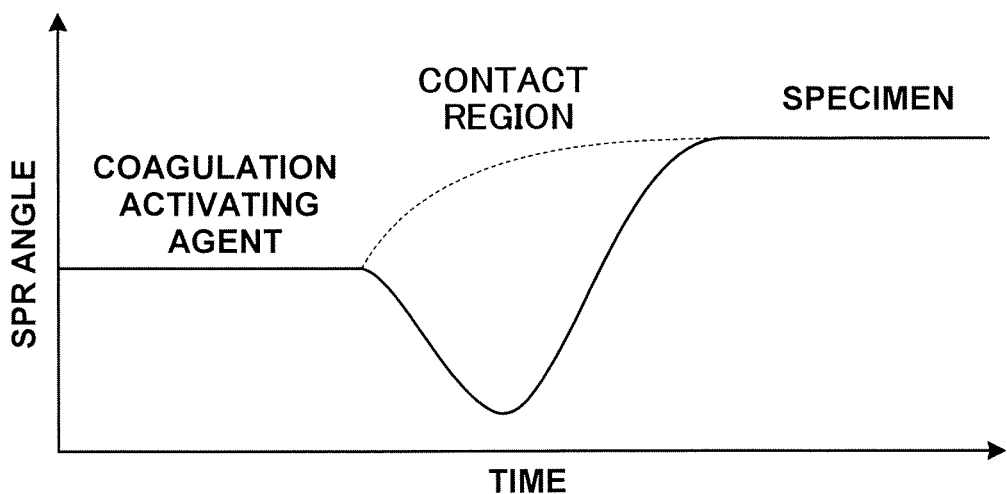
FIG. 4 is a graph showing a change in refractive index measured while the coagulation activating agent 211 and the specimen 212 flow in the micro flow channel 204 when coagulation reaction occurs.

An embodiment of the present invention will be described below. FIG. 1 is a flowchart for explaining a blood coagulation test method according to the embodiment of the present invention. First of all, in step S101, a specimen containing blood plasma and a coagulation activating agent are introduced into a flow channel, with the coagulation activating agent being positioned ahead, in a state in which portions arrayed in series in the extending direction of the flow channel flow in contact with each other (first process). The flow channel is, for example, a micro flow channel formed in a measurement chip used while being attached to a surface plasmon resonance measurement apparatus.

In step S102, in the process in which the coagulation activating agent, the contact region between the coagulation activating agent and the specimen, and the specimen pass through a measurement portion provided midway along the flow channel in the order named, the refractive indices of the coagulation activating agent and the contact region are measured in a time-series manner (second process). In step S103, the blood coagulation ability of the specimen is measured by comparing the first refractive index value which is the refractive index of the coagulation activating agent with the second refractive index value which is the minimum refractive index of the contact region, among the results obtained by time-series measurement (third process).

In the measurement chip used in the above surface plasmon resonance measurement apparatus, an Au layer is formed on the measurement portion, located midway along the micro channel flow, on the measurement apparatus side. As is known well, in surface plasmon resonance measurement, the refractive index of a liquid in contact with the above measurement region is measured from the intensity of the reflected light of light with which the lower surface of the measurement region is irradiated. On the surface of the Au layer in contact with the liquid, a valley is observed, where the refractive index decreases at an angle at which an evanescent wave resonates with a surface plasmon wave. The surface plasmon resonance angle at which this resonance occurs depends on the refractive index of the liquid which comes into contact with the Au layer. Therefore, a change in the refractive index of a liquid passing through the measurement region of the flow channel is obtained from a change in the intensity of reflected light measured.

In the measurement in step S102, first of all, the refractive index of the coagulation activating agent is measured as an almost constant value (first refractive index value) until the coagulation activating agent passes through the measurement portion. In contrast to this, the refractive index of the contact region decreases once and then increases in the process in which the contact region passes through the measurement portion. Thereafter, the refractive index of the specimen is measured as a constant value until the specimen passes through the measurement region. The contact region can be classified into a region near the coagulation activating agent, a middle region, and a region near the specimen. Of these regions, the middle region has a portion where the refractive index becomes minimum. It is possible to measure the blood coagulation ability of the specimen by comparing the first refractive index value with the refractive index (second refractive index) of the portion where the refractive index becomes minimum.

How it is possible to measure the blood coagulation ability of a specimen (blood plasma) from the first and second refractive index values will be described in more detail below.

First of all, as shown in FIG. 2, when a coagulation activating agent 211 and a specimen 212 flow in series in a micro flow channel 204 formed between a substrate 201 and a flow channel substrate 203, the coagulation activating agent 211 and the specimen 212 are mixed by diffusion at a contact region 213 as the boundary portion between them. Note that FIG. 2 shows a state in which an Au layer 202 is formed on the substrate 201.

While these two liquids are supplied in series, when no chemical reaction occurs between the two substances, an intermediate composition between the two liquids simply appears in the contact region 213. For example, when the coagulation activating agent 211 causes no coagulation reaction in the specimen 212, an intermediate composition between the coagulation activating agent 211 and the specimen 212 appears in the contact region 213. Since blood plasma or a biochemical reagent contains proteins in a large amount, the generally measured refractive index of the solution becomes larger than that of the coagulation activating agent. For this reason, when no coagulation reaction occurs, the refractive index measured while the coagulation activating agent 211 and the specimen 212 flow in the micro flow channel 204 changes as shown in FIG. 3.

As shown in FIG. 3, as the measurement time elapses, the refractive index of the coagulation activating agent 211 is measured at first. Subsequently, in measurement in the contact region 213, the refractive index of an intermediate composition between the coagulation activating agent 211 and the specimen 212 gradually approaches that of the specimen 212. Thereafter, the refractive index of the specimen 212 is measured. In this case, since the refractive index of the specimen 212 greatly depends on the concentration of a protein, different blood plasma components greatly differ in their measured refractive index values.

On the other hand, when the coagulation activating agent 211 causes a coagulation reaction in the blood plasma contained in the specimen 212, the refractive index in the contact region 213 changes differently from the above state. For example, in the contact region 213 between the specimen 212 containing blood plasma and the coagulation activating agent 211, the thromboplastin contained in the coagulation activating agent 211 converts the prothrombin contained in the blood plasma of the specimen 212 into thrombin to start a coagulation reaction. This causes a biochemical reaction by which the produced thrombin converts the fibrinogen contained in the blood plasma into fibrin as an insoluble protein. Furthermore these fibrins form a polymer to produce a thrombus.

Observing a change in refractive index in the contact region 213 in this manner leads to the observation of a region whose refractive index is lower than those of the coagulation activating agent 211 and the specimen 212, as shown in FIG. 4. This phenomenon is considered to be caused by lift force (Saffman force) originating from the circulating flow generated around particles 221 formed in a flow in the contact region 213 exhibiting a large velocity gradient when particles flow in the straight micro flow channel 204.

Assume that a spherical particle having a diameter d is moved by lift force in a direction perpendicular to a flow. In this case, when the fluid resistance acting on the particle is expressed by Stokes' law of resistance, a moving velocity $v_p$ of the particle is expressed by Saffman's expression as follows:

$$v_p = \frac{81.2}{12\pi} \frac{d}{v^{0.5}} (u - u_p) \sqrt{\frac{du}{dy}} \quad (1)$$

In equation (1), v is the dynamic viscosity coefficient of a liquid, u is the average velocity of the liquid in the flow direction, and $u_p$ is a particle velocity in the flow direction. According to equation (1), if the particle velocity in the flow direction is equal to the average velocity of the liquid in the flow direction ($u_p=u$), the movement of the particle due to the lift force can be neglected. If, however, the particle velocity is different from the fluid velocity, the movement of the particle due to the lift force cannot be neglected. If the particle velocity is higher than the fluid velocity, the particle moves toward the wall of the flow channel. On the other hand, if the particle velocity is lower than the fluid velocity, the particle moves in the main flow direction. For this reason, if the particle velocity is different from the fluid velocity, the particle moves outside the contact region as a boundary layer.

The particle velocity is influenced by the driving force and resistive force received from the flow velocity of the fluid substance (fluid). As a resistive force which an object (particle) in a fluid receives from the flowing fluid, the resistive force expressed by Newton's resistance law given below is known.

$$D = \frac{1}{2} \rho C d S V^2 \quad (2)$$

In equation (2), ρ is the density of a liquid, Cd is an effectiveness factor, S is the projection area of an object, and V is a velocity. According to equation (2), as the projection area increases with an increase in the size of the object in the fluid, the resistive force of the object against the fluid increases. This decreases the particle velocity, and hence increases the Saffman force. The increase in Saffman force will increase the force to move the particle to the central portion of the flow channel in which the flow velocity is high.

In addition, a substance in the liquid is influenced by a buoyancy force. A buoyancy force $F_b$ is expressed by "$F_b=\rho_f Vg$" where $\rho_f$ is the density of the fluid, V is the volume of the object, and g is a gravitational acceleration. Therefore, as the surface area of the object increases, the buoyancy force increases. This increases the force to separate from the inner wall of the flow channel.

As the two liquids, i.e., the coagulation activating agent and the specimen, move forward and the coagulation reaction on the interface between the liquids progresses, insoluble fibrin increases in amount. In addition, polymerization rapidly increases the volume. For this reason, as shown in FIG. 2, the particles 221 formed from fibrin which has acquired a particle velocity lower than the fluid velocity move to the central portion of the micro flow channel 204 without settling down on the Au layer 202 as the inner wall of the micro flow channel 204. As a result of the above process, on the Au layer 202 (inner wall portion) of the measurement portion, it is thought that a decrease in refractive index is observed as the refractive index of a component in the contact region 213 which is a residue after rapid consumption of surrounding fibrin is reflected in the measurement result.

Example

Figure 5:
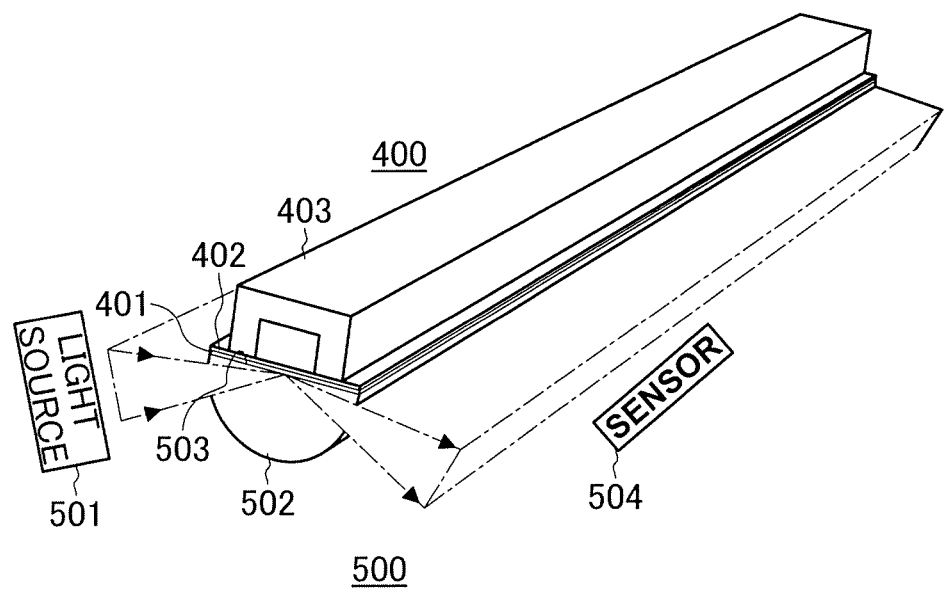
FIG. 5 is a perspective view showing the arrangements of a measurement chip 400 and an SPR apparatus 500.
Figure 6:
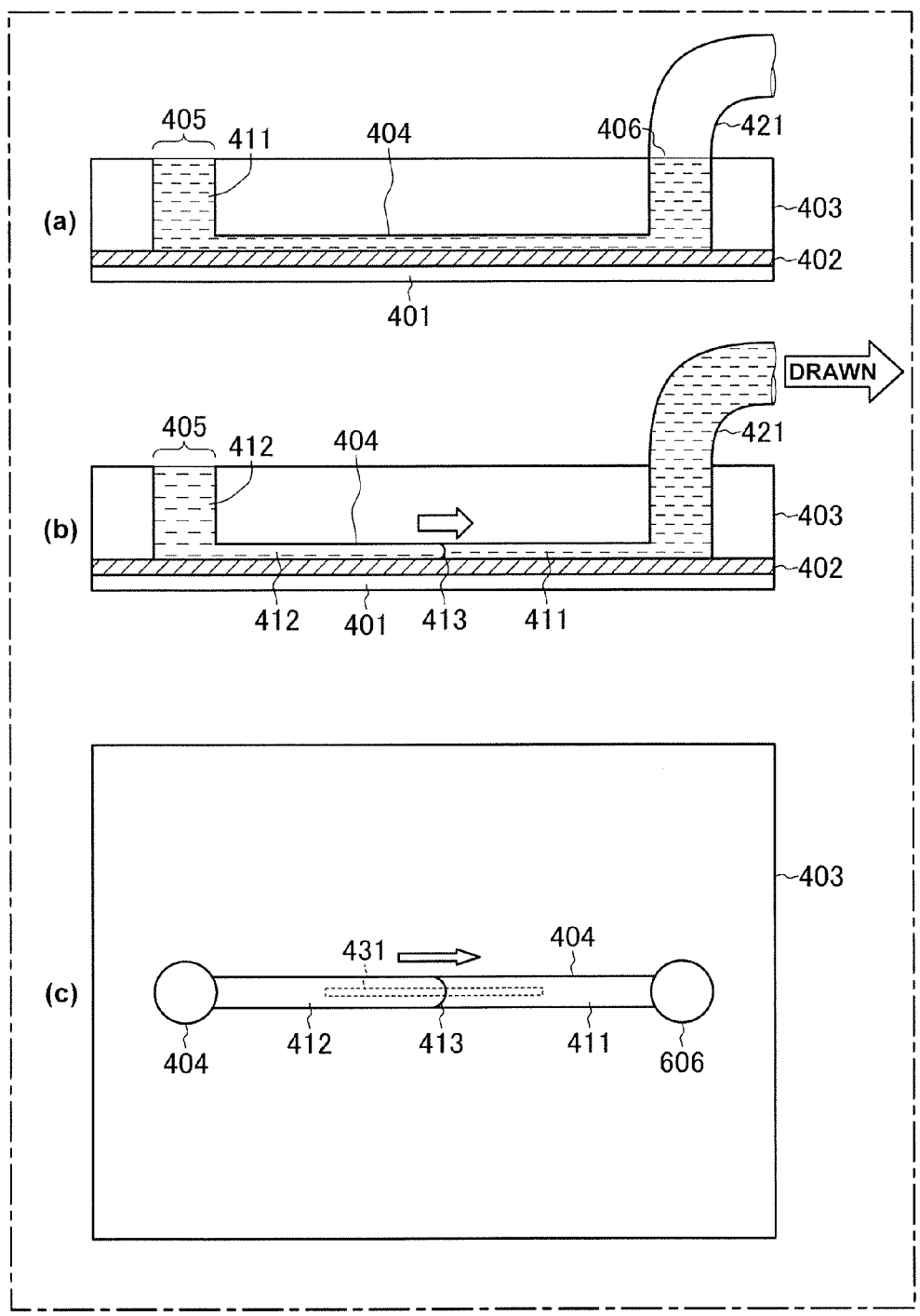
FIG. 6 shows sectional views (a) and (b) and a plan view (c) showing the arrangement of the measurement chip 400.

An example will be described in more detail below. A measurement chip 400 and an SPR apparatus 500 used for measurements will be described first. As shown in FIGS. 5 and 6, the measurement chip 400 includes a substrate 401 formed from BK7 glass, an Au layer 402 having a thickness of about 50 nm, and a flow channel substrate 403. The Au layer 402 can be formed by a well known deposition technique such as a sputtering method.

In addition, the flow channel substrate 403 includes a groove portion serving as a micro flow channel 404, an inlet port 405, and an outlet port 406. For example, the flow channel substrate 403 can be formed from polydimethylsiloxane (PDMS). The groove portion can have a depth (height) of about 50 μm. The inlet port 405 had an aperture of 3 mm. The outlet port 406 had an aperture of 1.5 mm. These ports can be formed by, for example, a well known biopsy trepan. In addition, the substrate 401 and the flow channel substrate 403 were separately fabricated. Finally, the measurement chip 400 was assembled such that the micro flow channel 404 overlaps the measurement region.

After the bonding surfaces of the substrate 401, on which the Au layer 402 was formed, and the flow channel substrate 403, in which the flow channel groove was formed, were activated by being irradiated with oxygen gas plasma (reactant ions), the respective bonding surfaces were brought into contact with each other and bonded to each other, thereby integrating the two substrates. Plasma irradiation is executed in the processing chamber of a plasma processing apparatus. Plasma was generated by microwaves with an output of 70 W. In addition, oxygen was supplied into the processing chamber at 100 sccm, and the oxygen partial pressure in the processing chamber was set to 10 Pa. Note that sccm is the unit of flow velocity, and indicates that a fluid of 0° C. and 1013 hPa flows at a rate of 1 cm$^3$/min. In addition, plasma irradiation was executed for about 5 sec.

In addition, a negative pressure mechanism 421 is connected to the outlet port 406. This makes it possible to draw (suck) the liquid in micro flow channel 404 through the outlet port 406. The negative pressure mechanism 421 includes, for example, a drain tank and a negative pressure pump (MFCS-VAC available from Fluigent) which are connected to each other through a stainless pipe.

In measurement, a matching oil (not shown) having the same refractive index as that of BK7 glass is applied onto a measurement surface 503 formed on a measurement prism 502 of the SPR apparatus 500, and the rear surface of the substrate 401 of the measurement chip 400 is arranged on the oil. In addition, the measurement region of the measurement chip 400 is arranged to overlap the optical axis of light emitted from a light source 501 of the SPR apparatus 500. The SPR apparatus 500 is, for example, "Smart SPR SS-100" available from NTT advanced technology.

The light emitted from the light source 501 is condensed to enter the prism 502, and irradiates the measurement region of the measurement chip 400 in tight contact with the measurement surface 503 of the measurement prism 502. The Au layer 402 is formed on a portion of the micro flow channel 404 which becomes the measurement region of the measurement chip 400, and the rear surface of the Au layer 402 is irradiated with the condensed light transmitted through the measurement chip 400.

The condensed light which has irradiated the rear surface in this manner is reflected by the rear surface of the Au layer 402 with which a fluid as a flow velocity measurement target is in contact. A sensor 504 formed from an image sensor such as a so-called CCD image sensor photoelectrically converts the light to obtain an intensity (light intensity). A change in refractive index is obtained from a change in light intensity obtained in this manner.

First of all, the micro flow channel 404 is filled with a PT coagulation reagent 411 (10 mL) as a coagulation activating agent. The capacity of the micro flow channel 404 is about 1 mL to 2 mL. As shown in (b) and (c) in FIG. 6, a specimen 412 (10 mL) formed from blood plasma can be introduced through the inlet port 405 in one end of the micro flow channel 404 filled with the PT coagulation reagent 411 and drawn through the outlet port 406 in the other end of the micro flow channel 404 with a constant pressure (negative pressure). The negative pressure mechanism 421 can be connected to the outlet port 406 to suck the PT coagulation reagent 411. With this operation, while the PT coagulation reagent 411 exits on the other side (inlet port 405 side) in the micro flow channel 404 and the specimen 412 exists on one end side (outlet port 406 side), the PT coagulation reagent 411 and the specimen 412 are transported to the other end inside the micro flow channel 404, with the trailing end of the PT coagulation reagent 411 being in contact with the leading end of the specimen 412.

In this case, in a contact region 413 in contact with the specimen 412 and the PT coagulation reagent 411, the PT coagulation reagent 411 is added to the specimen 412, and hence a coagulation reaction can occur in the contact region 413. For this reason, as described above, when the contact region 413 is formed in a state in which the PT coagulation reagent 411 and the specimen 412 flow in the micro flow channel 404 while being arrayed, a coagulation reaction starts in the contact region 413.

As described above, while the leading end of the specimen 412 comes into contact with the trailing end of the PT coagulation reagent 411 to form the contact region 413 and the specimen 412 and the PT coagulation reagent 411 flow in the micro flow channel 404 as shown in FIG. 6, a change in the refractive index (SPR angle) of the fluid in the micro flow channel 404 is measured. The SPR angle is measured in a predetermined measurement region 431 in the micro flow channel 404. In this measurement of the SPR angle, a change in the SPR angle is measured when the contact region 413 passes through the measurement region 431. The detection region of the sensor 504 corresponds to the measurement region 431. A plurality of photodiode elements are arranged side by side in the flow direction in the detection region of the sensor 504. In the measurement region 431, a change in light intensity (SPR angle) is measured at the position of each photodiode element (each pixel position).

Let n be the refractive index of the substrate 401, εm be the dielectric constant of the Au layer 402, εS be the dielectric constant of the sample, and θ be the incident angle of light striking the interface between the substrate 401 and the Au layer 402. In this case, when "$n(\omega/c)\sin\theta = (\omega/c)[\varepsilon m \times \varepsilon s/(\varepsilon m + \varepsilon s)]^{1/2}$ . . . (1)" holds, the plasmons induced at the incident angle and the interface between the substrate 401 and the Au layer 402 resonate (see non-patent literature 1). The angle θ is an SPR angle.

In addition, when plasmon resonance occurs, since reflected light is attenuated, this state appears as a change in the value detected by any of the photodiode elements of the sensor 504. Therefore, an SPR angle is obtained based on the pixel position (pixel value) of the photodiode element whose detected light intensity has decreased. As a result, a refractive index is obtained. For example, with the above pixel value, a refractive index value is obtained by a conversion formula like "refractive index value=pixel value×$1.2739 \times 10^{-4}$+1.3188 (light source wavelength: 770 nm)".

Figure 7:
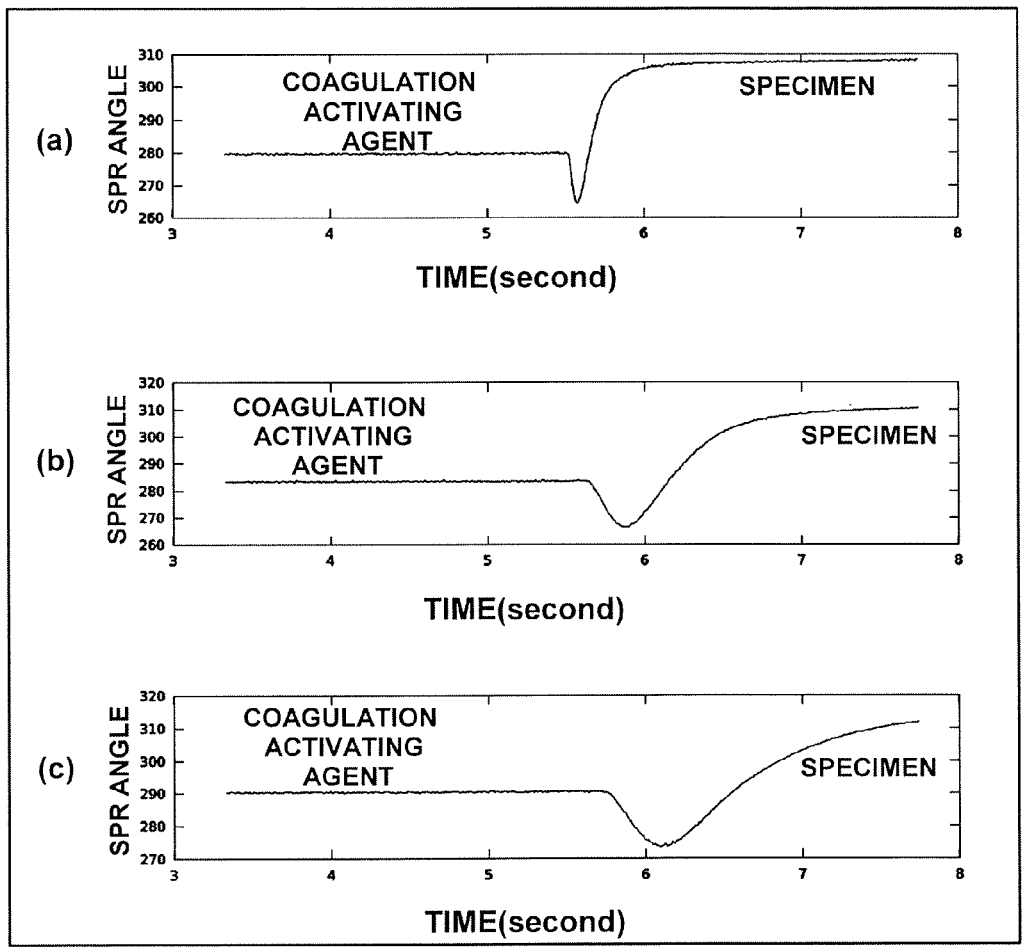
FIG. 7 shows graphs showing SPR angle changes measured in the process of a contact region 413 passing through a measurement region 431.

Measurement results in the above example will be described. First of all, FIG. 7 shows changes in SPR angle at three observation points in the measurement region 431. FIG. 7 shows graphs each showing a change in SPR angle measured in the process of the contact region 413 passing through the measurement region 431. Referring to FIG. 7, pixel values indicating the positions of pixels in the image sensor (imaging device) in the SPR apparatus used for measurements are used as substitutes for "SPR angle" on the ordinate.

In FIG. 7, (a) indicates the detection result obtained by the first photodiode element of the sensor 504. In FIG. 7, (a) indicates the detection result obtained at the start end on the inlet port 405 side of the measurement region 431.

In FIG. 7, (b) indicates the detection result obtained by the 240th photodiode element of the sensor 504. In FIG. 7, (b) indicates the detection result obtained at the middle of the measurement region 431.

In FIG. 7, (c) indicates the detection result obtained by the 480th photodiode element of the sensor 504. In FIG. 7, (c) indicates the detection result obtained at the finish end on the outlet port 406 side of the measurement region 431.

As shown in FIG. 7, obviously, a low refractive index region appears in a contact region in which a transition occurs between the refractive index of a coagulation activating agent and the refractive index of a specimen (blood plasma) at each measurement point.

Figure 8:
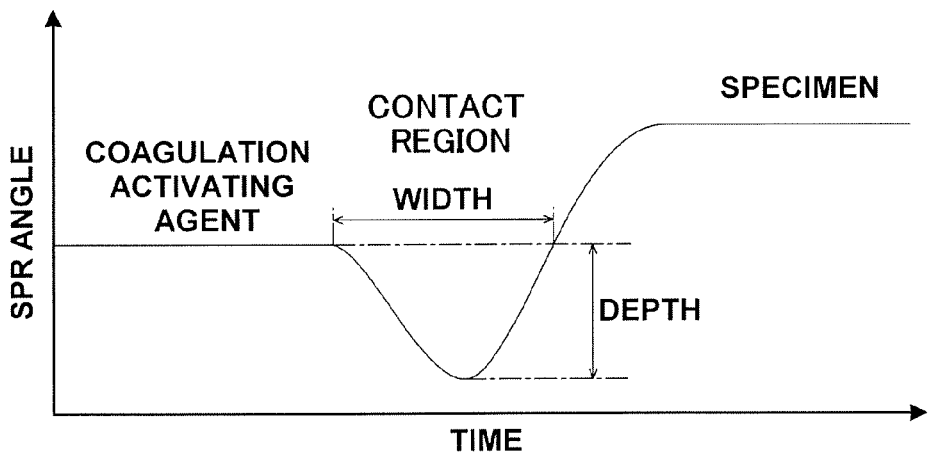
FIG. 8 is a graph for explaining parameters of width and depth set with respect to a contact region whose refractive index has decreased.

In this case, as shown in FIG. 8, parameters of width and depth are set with respect to a contact region whose refractive index has decreased. A depth is the minimum second refractive index measured in the contact region when viewed from the first refractive index value which is the measured refractive index of a coagulation activating agent, and is given by "first refractive index value−second refractive index value". For this reason, the larger the difference between the first and second refractive index values, the larger the depth value.

Figure 9:
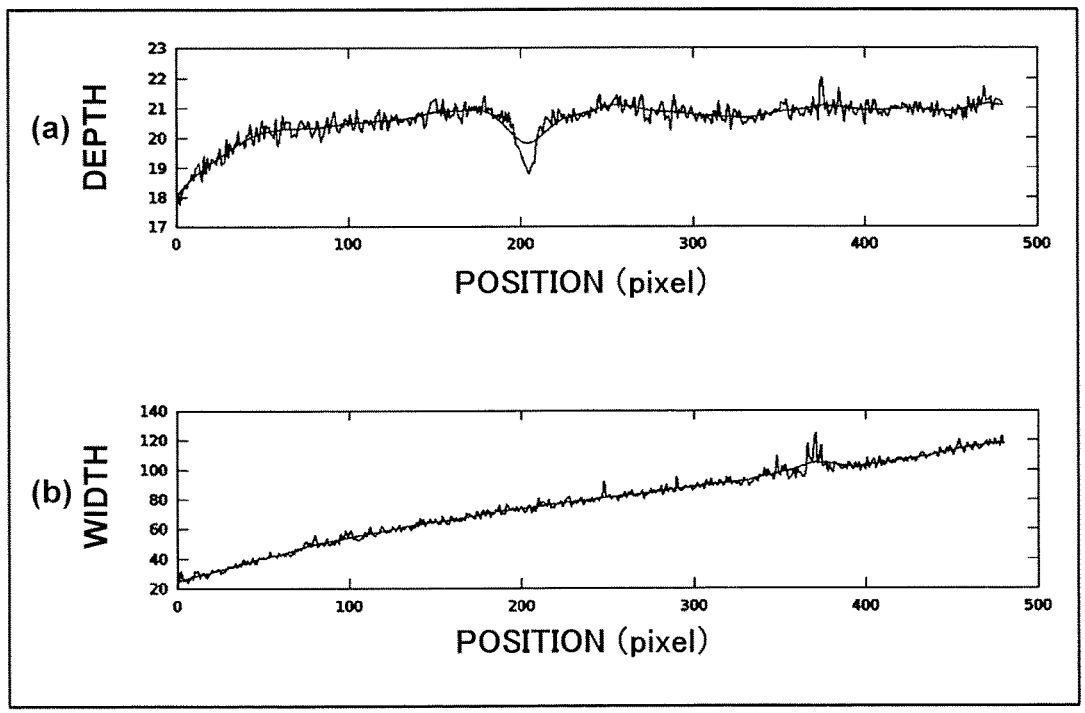
FIG. 9 shows graphs showing changes in parameters of depth (a) and width (b) in correspondence with positions (pixels) on a measurement region which are made to correspond to the positions of a plurality of photodiode elements constituting a sensor 504.

FIG. 9 is a graph showing changes in parameters of depth (a) and width (b) which correspond the positions (pixels) in the measurement region which are made to correspond to the positions of a plurality of photodiode elements constituting the sensor 504.

As indicated by (a) in FIG. 9, the value of depth increases from the start point of the contact region to the outlet port side (downstream), and becomes maximum at the middle point of the contact region. "Width" indicated by (b) in FIG. 9 monotonically increases along the movement (flow) of the contact region. In contrast to this, "depth" indicated by (a) in FIG. 9 tends to be saturated after reaching a predetermined value after a given position (downstream) during the movement of the contact region. That is, it is thought that the process of a coagulation reaction occurring in the contact region is reflected in this tendency. For this reason, a depth (first refractive index value−second refractive index value) represents a numerical value dependent on coagulation activity, and hence can be an index.

Figure 10:
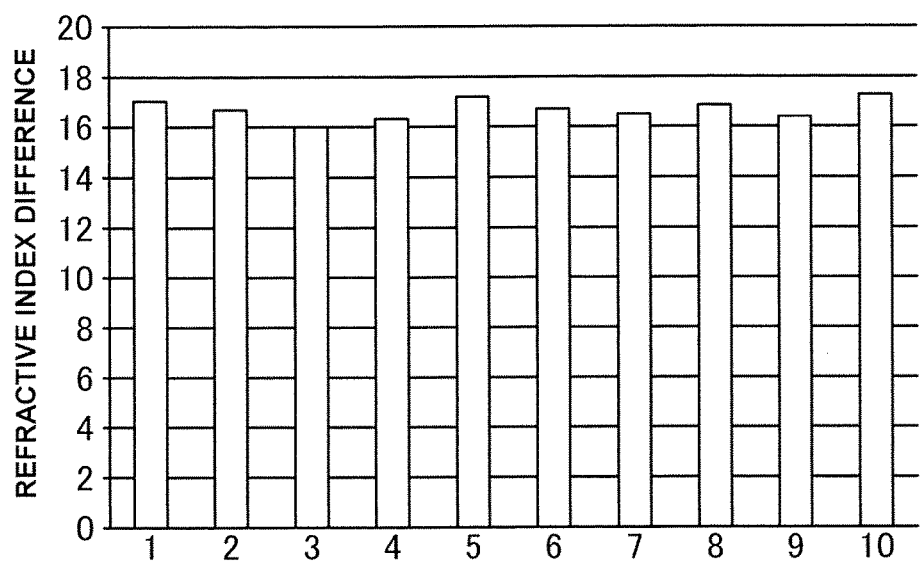
FIG. 10 is a graph showing the results of repeated measurements in an experiment using a standard specimen (activity ratio: 86%) and a 75% PT coagulation activating agent as depths (second refractive index values and first refractive index values)

FIG. 10 is a graph showing the results obtained by repeated measurements in an experiment using a standard specimen (activity ratio: 86%) and a 75% PT coagulation activating agent as refractive index differences (first refractive index values−second refractive index values). The micro flow channel was cleaned only by making an alkaline cleaning solution flow therethrough once between the respective measurements. As shown in FIG. 10, as a result of 10 consecutive measurements, variations in measurement value (valley depth) could be suppressed as low as CV=2.4%.

Figure 11:
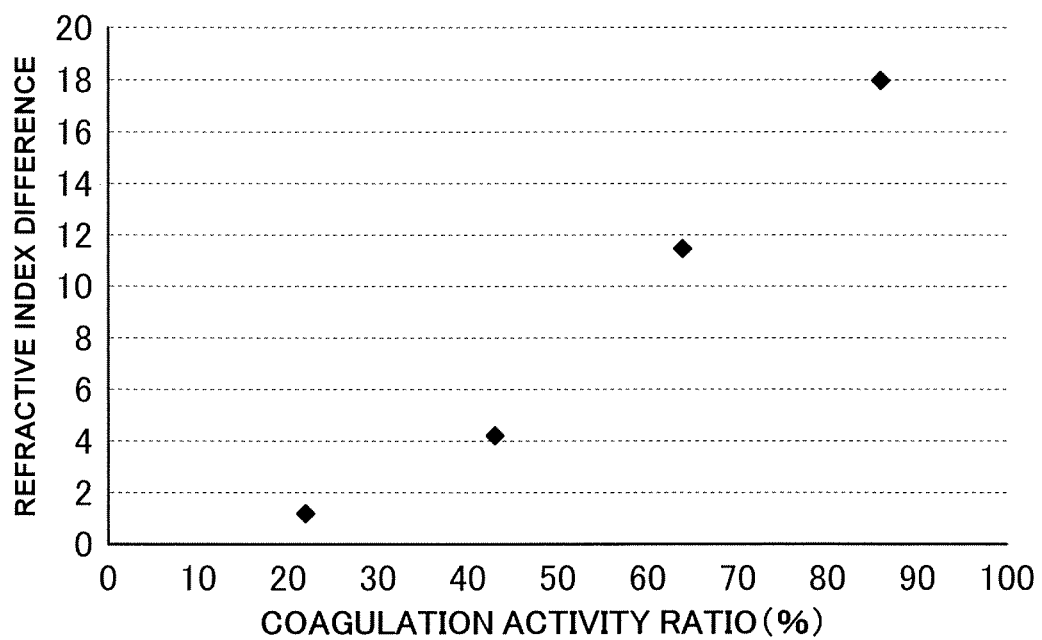
FIG. 11 is a graph showing the calibration curve generated from the results (depths) measured by measurements according to the above embodiment upon preparing specimens with different activity ratios (64%, 43%, and 22%) by diluting the standard specimen (activity ratio: 86%) with a thinner.

The standard specimen (activity ratio: 86%) was diluted with a thinner to prepare specimens with different activity ratios (64%, 43%, and 22%), and a calibration curve was generated from the results (refractive index differences) obtained by measurements in the above embodiment. FIG. 11 is a graph showing the generated calibration curve. Note that "refractive index difference" on the ordinate of FIG. 11 corresponds to "depth" described with reference to FIG. 8. Referring to FIG. 11, pixel value differences in the image sensor (imaging device) in the SPR apparatus used for measurements are used as substitutes for "refractive index difference" on the ordinate.

In this case, since a portion of the contact region in which the refractive index decreases is greatly influenced by the refractive index of a composition other than fibrin as a specimen component, if a low refractive index solution such as water is used as a thinner, the diluted portion is added to the depth. For this reason, in measurements for obtaining the above calibration curve, a glucose solution having the same refractive index as that of the standard specimen was used as a thinner. In addition, as a coagulation activating agent, a 75% PT coagulation activating agent was used.

It could be confirmed as a result of the generation of the calibration curve that as the specimen activity ratio increased, the difference between the first and second refractive index values increased. This can be because the difference between the first and second refractive index values greatly depends on the consumption of fibrin, and a highly active specimen in which a large amount of fibrin is produced becomes lower in refractive index than the entire low refractive index region.

As described above, according to the present invention, in the process of making a coagulation activating agent, a contact region, and a specimen pass through a micro flow channel in the order named, the refractive indices of the coagulation activating agent and the contact region are measured in a time-series manner, and the blood coagulation ability of the specimen is measured by comparing the first refractive index value as the measured refractive index of the coagulation activating agent with the second refractive index value as the minimum refractive index of the measured refractive indices of the contact region. This makes it possible to test more accurate blood coagulation ability by a blood coagulation test using the micro flow channel.

According to the present invention, since measurement is robust against the influence of flow velocities, a measurement cell or micro flow channel, which has conventionally been designed to be subjected to hard cleaning upon removal or be disposable, can be repeatedly used. This makes it possible to achieve a reduction in cost. In addition, the present invention is configured to only measure the refractive indices of the coagulation activating agent and contact region passing through a flow channel, and hence the time required for measurement is very short. This makes it possible to perform measurement more quickly.

Note that it is obvious that the present invention is not limited to the embodiments described above, and many modifications and combinations can be implemented within the technical idea of the present invention by those who have usual knowledge in this field. For example, it is possible to perform other coagulation measurement methods in the same manner, as well as PT tests, by using a coagulation activating agent which produces fibrin. For example, it is possible to cope with an APTT (Activated Partial Thromboplastin Time) test by using the specimen obtained by mixing a specimen with an APTT coagulation activating agent and calcium chloride as a coagulation activating agent. In addition, it is possible to cope with a coagulation activating agent fibrinogen (Fib) concentration test by using a specimen without any change and a thrombin coagulation activating agent as a coagulation activating agent.

In addition, the time-series refractive index (refractive index change) measurement to be performed is not limited to surface plasmon resonance measurement, and total reflection measurement may be used. When, for example, a measurement region in a micro flow channel is kept transparent without forming any Au layer, the incident angle (critical angle) at which total reflection occurs at the transparent portion on the lower surface of the flow channel can be measured as an index value for refractive indices.

EXPLANATION OF THE REFERENCE NUMERALS AND SIGNS

201 . . . substrate, 202 . . . Au layer, 203 . . . flow channel substrate, 204 . . . micro flow channel, 211 . . . coagulation activating agent, 212 . . . specimen, 213 . . . contact region, 221 . . . particle.

The invention claimed is:

1. A blood coagulation test method comprising:
a first step of introducing a specimen containing blood plasma and a coagulation activating agent into a flow channel, with the coagulation activating agent being positioned ahead, in a state in which portions arrayed in series in an extending direction of the flow channel flow in contact with each other;
a second step of measuring refractive indices of the coagulation activating agent and refractive indices of a contact region between the coagulation activating agent and the specimen at a predetermined measurement position provided midway in the flow channel in a time-series manner in the process in which the coagulation activating agent, the contact region, and the specimen pass through the predetermined measurement position in the order named;
a third step of identifying, from the refractive indices measured in a time-series manner at the predetermined measurement position in the second step, a first refractive index value which is the measured refractive index of the coagulation activating agent and a second refractive index value which is the minimum refractive index value out of the measured refractive indices of the contact region; and
a fourth step of measuring blood coagulation ability of the specimen by comparing the first refractive index value with the second refractive index value.

2. A blood coagulation test method according to claim 1, wherein a surface plasmon resonance angle measured by surface plasmon resonance measurement at the measurement portion is used as the refractive index value.

* * * * *